Figure 1:
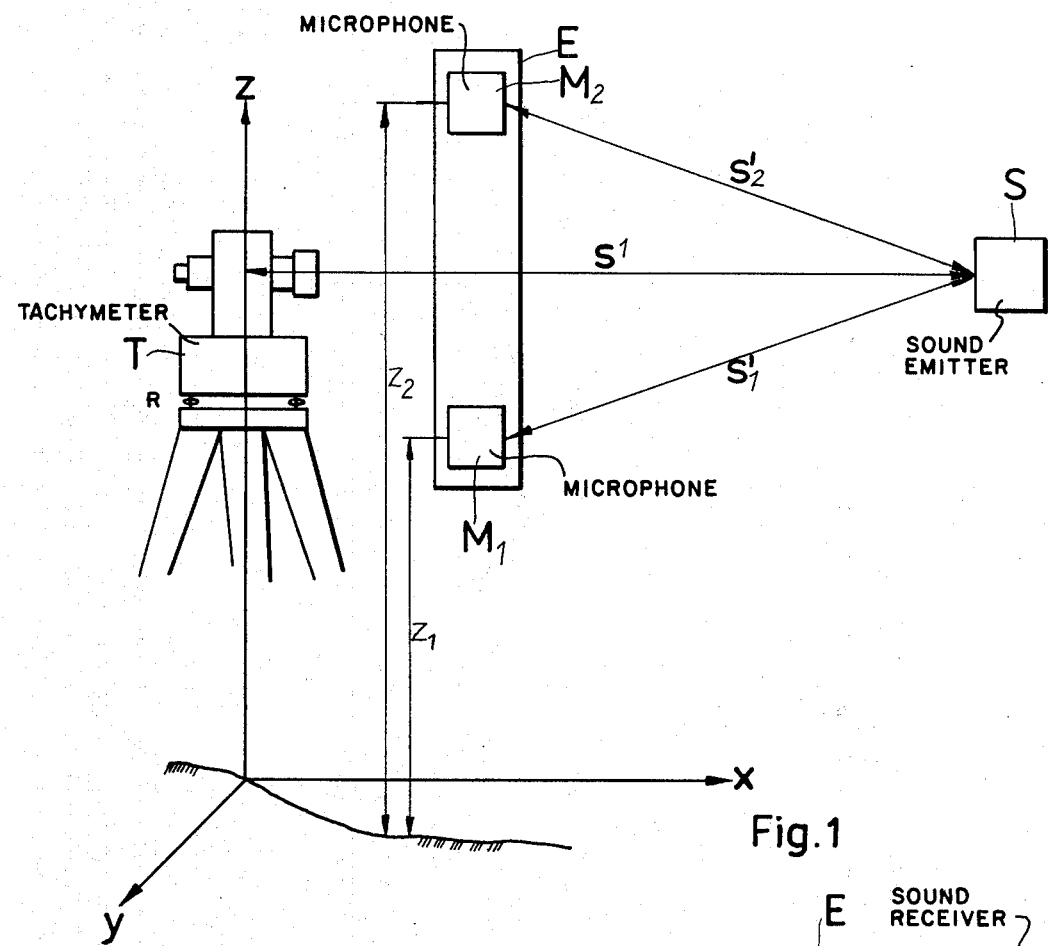

United States Patent [19]

Stegmann et al.

[11] 4,347,739
[45] Sep. 7, 1982

[54] MEASURING EQUIPMENT FOR THE DETERMINATION OF TERRESTRIAL REFRACTION

[75] Inventors: Horst Stegmann; Wolfgang Meyl; Peter Hentschel, all of Dresden, German Democratic Rep.

[73] Assignee: Jenoptik Jena GmbH, Jena, German Democratic Rep.

[21] Appl. No.: 153,344

[22] Filed: May 27, 1980

[51] Int. Cl.³ ............................................. G01W 1/00
[52] U.S. Cl. ................................. 73/170 R; 33/275 R
[58] Field of Search .......................... 73/170 R, 861.29; 33/275 R, 292; 356/128

[56] References Cited

U.S. PATENT DOCUMENTS 3,446,559 5/1969 Astheimer et al. ................. 356/128
4,031,756 6/1977 Rotier et al. ................. 73/861.27 X
4,112,756 9/1978 MacLennan et al. ............ 73/597 X Primary Examiner—Jerry W. Myracle
Attorney, Agent, or Firm—Jordan and Hamburg

[57] ABSTRACT

A measuring arrangement is described for determining the terrestrial refraction in geodetic measurements, (such as trigonometric height transfers when staking out and for precision tachymetry, controlling devices for building machinery using a laser beam, and precision levelling). The measuring arrangement includes a geodetic measuring instrument, an electronic calculator and a device for measuring differences of travel times of soundwaves. After the soundwaves produced by a sound emitter have traversed representative airlayers (for instance at different heights), the time difference is measured and is used for calculating the refraction.

13 Claims, 2 Drawing Figures

MEASURING EQUIPMENT FOR THE DETERMINATION OF TERRESTRIAL REFRACTION

BACKGROUND OF THE INVENTION

This invention relates to measuring equipment for determining terrestrial refraction when making geodetic measurements. The invention is particularly useful in geodetic engineering for staking out by means of an electronic tachymeter, when designed heights must be trigonometrically transferred. The invention is particularly useful in precision tachymetry, for precise levelling and for the control of building machinery, for example by means of an active collimating ray (laser beam).

It is known that the refraction of air layers close to the ground cannot be provided with the reliability needed for practical use. The cause of refraction is the variable state of the airlayers. Many studies have shown that a strong correlation exists between the deviation of the collimating ray and the vertical gradient of temperature, so that the coefficient of refraction can be determined mainly as a function of the temperature gradient.

When transferring heights trigonometrically, the influence of the refraction may be substantially eliminated by simultaneously measuring the opposing angles of zenith. A residual error, though, may still occur as a consequence of varying coefficients of refraction at both endpoints. In the unilateral trigonometrical transfer of heights, as may be the case when staking out, for precision tachymetry and for the regulation of building machinery by means of an active collimating ray, the values of measurement are subject to refraction. In order to determine the effective coefficient of refraction as nearly as possible, the gradient of temperature along the path of light between the geodetic instrument and the sighting point should be known. Close to the earth's surface the path of light may be defined approximately as an arc and the gradient of temperature may be calculated based upon measurements of difference of temperature between points of differing height near the base of the instrument and, in order to improve the results, also additively by measuring differences of temperature at points near the sighting point. Additional measurements of differences of temperature at discrete points in the direction of the collimating ray have been undertaken in scientific studies. Such measurement arrangements employing several stations for the measurement of temperature differences between the basepoint and the point of sight are too expensive for practical purposes, because they must be constantly reconstructed since the points of sight are usually located in various directions.

It is known that variations of refraction occur, depending on the distance from the point of sight. Thus an observer may visibly expect that the accuracy of a geodetic instrument decreases with increasing distance from the geodetic instrument when averaging different adjacent local coefficients of refraction. In other words, for the determination of a probable coefficient of refraction, the local coefficients of refraction at the point of view influence the deviation of the collimating ray much more than those further afield. The known method of determination of angles of refraction by using the dispersion effect requires the use of very complicated instruments and can scarcely be of any use in airlayers close to the ground, due to the turbulence in this region.

SUMMARY OF THE INVENTION

The object of the invention is to determine terrestrial refraction, in geodetic engineering and construction engineering work, more exactly than possible heretofore.

The invention is based upon the provision of measuring means that render it possible to continually determine measuring values, starting at a determined range from the locus of the instrument, thereby allowing the calculation of the refraction at any instant. According to the invention this is achieved by directing a sound wave of fixed frequency to traverse each individual measuring distance between the geodetic instrument and the sighting point, or another representative distance having an appropriate orientation. The relation between the speed of sound and the condition of the air permits the determination of the respective refraction.

The invention is based upon the fact that the travel times of soundwaves having identical path lengths differ when air layers of different temperatures are traversed.

The measuring equipment for the determination of the terrestrial refraction according to the invention is comprised of a geodetic measuring instrument, an electronic calculating device and either a device V 1, according to the invention or a device V 2, according to the invention. The device V 1 of the invention serves to measure the difference of travel times of sound waves. It includes a sound emitter S and a sound receiver E, FIG. 2. The sound emitter S is provided with a pulse generator 1 and an electro-acoustical transducer 2. The sound receiver E includes 2 microphones $M_1$ and $M_2$ and a circuit for measuring and indicating the difference of the travel times. The two microphones $M_1$ and $M_2$ may be affixed to the geodetical measuring instrument vertically one above the other at various heights, or alternatively may be disposed in its immediate vicinity. If the two microphones are disposed in horizontal alignment they may alternatively be used to determine the horizontal component of refraction. The sound emitter may be combined with the reflector of the tachymeter device, or it may be positioned to be stationary at a place which is representative for the determination of the coefficient of refraction.

The spatial position of the microphones $M_1$ and $M_2$ and of the sound emitter S may be determined by spatial polar addition. The inclined (to one another) paths $s_1'$ and $s_2'$, FIG. 1, between the sound emitter S and the microphones $M_1$ and $M_2$ may be calculated by means of the electronic calculating unit (not shown).

The electroacoustic transducer 2 converts the electrical pulses created by the pulse generator 1 into sound pulses. The sound pulses, emitted by the sound emitter S traverse the inclined paths $s_1'$ and $s_2'$. The sound pulses arrive at the microphones $M_1$ and $M_2$ at different times when the vertical temperature gradients vary along these paths. This difference is measured in the circuit and displayed. The difference of traversing times, their mean value or a representative value for the varying temperature fields, traversed by the sound, serves to derive the present means vertical gradient of temperature in the path from the sound emitter S to the sound receiver E. The real time coefficient of refraction may be calculated from the gradient of temperature by means of the electronic calculator, using known mathematical correlations.

The device V 2 of the invention has the same function as the device V 1. In the device V 2 the sund emitter S includes a pulse generator 1 and two electro-acoustical transducers 2, arranged vertically one above the other.

BRIEF FIGURE DESCRIPTION

Figure 2:
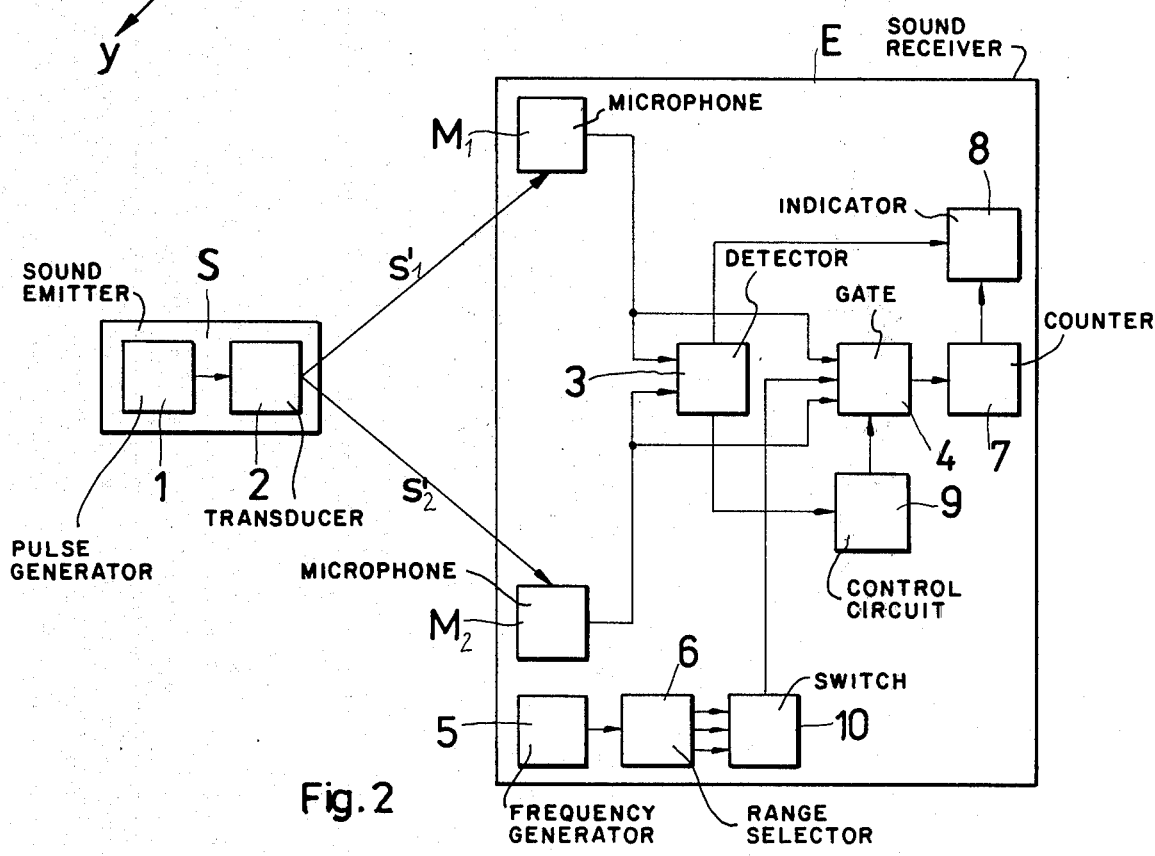

The measuring arrangement for determining terrestrial refraction is disclosed below with reference to the drawings wherein:

FIG. 1 is a schematic of the measuring device for determining vertical refraction; and FIG. 2 is a schematic block diagram of the device V 1 for measuring the travel time differences of sound.

DETAILED DISCLOSURE OF THE INVENTION

The measuring arrangement for determination of the vertical refraction, in accordance with the invention, includes an electronic tachymeter T with an electronic calculator and a device V 1, according to the invention, consisting of a sound emitter S and a sound receiver E, as shown in FIG. 1. The sound emitter S may be either stationary at a determined distance from the locus of the instruments (for instance 200 to 300 meters in the main direction of staking out) or, for not too large measuring paths s' (depending on the power of the sound emitter S), it may be set up to have a variable position, together with the reflector of the equipment of the tachymeter. The sound receiver E is provided with two microphones $M_1$ and $M_2$, vertically one above the other at elevations $z_1$ and $z_2$ above the surface of the earth, and either fastened directly to the electronic tachymeter T itself or disposed in its immediate vicinity. The sound receiver E includes both microphones $M_1$ and $M_2$ with amplifiers, detector 3 for the first pulse, a gate circuit 4, a frequency generator 5, a range selector 6, a counter 7, a numerical indicator 8, a control 9 and a switch 10. In an x,y,z-coordinate system (e.g., a local system with the plumbline at the locus of the instrument defining the z-axis, the direction of the x-axis being the null-direction of the horizontal circle, and the origin being the point of traverse of the z-axis through the surface of the earth) the position of the microphones $M_1$ and $M_2$ and also of the sound emitter part S may be determined by spatial polar addition. The included paths $s_1'$ and $s_2'$ between the microphones $M_1$ an $M_2$ and the sound emitter S can be calculated by means of the electronic calculator. When the pulses emitted by the sound emitter S traverse fields of differing temperatures along the inclined paths $s_1'$ and $s_2'$, they arrive with different travel times at the sound receiver E. This difference of the travel times is measured exactly and used as an input quantity for the calculation of the means coefficient of refraction according to known relations of sound propagation in air and the derivation of the coefficient of refraction from the temperature gradient. The sound emitter S, for instance may be constructed such that the pulse generator 1 produces pulses of 1 to 2 msec duration with a pause of 250 msec. The microphones $M_1$ and $M_2$ with amplifiers convert the sound pulses into electrical pulses and amplify them. The "+" or "−" sign of the difference of travel times of the sound pulses (sign of the mean difference of temperatures between the inclined paths $s_1'$ and $s_2'$) is registered by the first pulse detector 3. The first pulse arriving at one of the microphones $M_1$ or $M_2$ opens the gate circuit 4, and the pulse arriving later through the other of the microphones $M_1$ and $M_2$ shuts the gate. When the gate circuit 4 is open the pulses, produced by the frequency generator 5 (e.g., having a frequency of 100 kHz), are capable of passing the gate. They are counted by the counter 7. The count content of the counter 7 is thus proportional to the difference of the travel times of the sound pulses and is indicated by the numerical register 8. The control circuit 9 resets the counter 7 back to zero, once about 200 msecs have passed. A range switch 6, which can be switched corresponding to different lengths of the measuring path s' by means of a switch 10 (for instance for s' = 100 m, 200 m, 300 m) apportions the frequency of the impulses of the impulse generator 5. This range selection allows the detection of differences of travel times from 0 to 990 μsec in steps of 10 μsec each, relative to a measuring path s' = 100 m. A difference of travel times of 10 μsec relates here to a difference of temperatures of 0.02° K.

The device V 2 of the invention may, in principle, be constructed in the same manner as device V 1. The sound emitter S for device V 2 is comprised of two electro-acoustical transducers 2 (for instance loudspeakers) arranged vertically one above the other at the same distance as the two microphones $M_1$ and $M_2$. They may be arranged to be movable on a leveling rod, so that, especially at horizontal sighting, the paths between the microphone $M_1$ and the lower electroacoustical transducer or between the microphone $M_2$ and the upper electroacoustical transducer are horizontal. The microphones $M_1$ and $M_2$ may be fastened to another leveling rod. The device V 2 may be used especially for precision leveling.

For sound velocities $v_{T1}$ and $v_{T2}$ at the absolute temperatures of gas $T_1$ and $T_2$ in one gas only:

$$\frac{v_{T1}}{v_{T2}} = \sqrt{\frac{T_1}{T_2}}.$$

The mean velocities of sound $\bar{v}_{T1}$ and $\bar{v}_{T2}$ at the mean air temperatures $\bar{T}_1$ and $\bar{T}_2$ in the inclined paths $s_1'$ and $s_2'$ can be calculated when the travel times $t_1$ and $t_2$ of the sound impulses are known.

$$\bar{v}_{T1} = \frac{s_1'}{t_1} \text{ and } \bar{v}_{T2} = \frac{s_2'}{t_2}.$$

With these values, the difference of travel times $\Delta t = t_2 - t_1$ and the mean difference of temperatures $\Delta \bar{T} = \bar{T}_2 - \bar{T}_1$, the upper equation is now:

$$\frac{s_1' \cdot t_2}{s_2' \cdot t_1} = \frac{s_1'}{s_2'}\left(1 + \frac{\Delta t}{t_1}\right) = \frac{\bar{T}_2 - \Delta \bar{T}}{\bar{T}_2} \approx \left(1 - \frac{\Delta \bar{T}}{2\bar{T}_2}\right).$$

The following equation results for the calculation of the mean difference of temperatures $\bar{T}$ upon the inclined paths $s_1'$ and $s_2'''$ $$\Delta \bar{T} \approx 2\bar{T}_2 \left[1 - \frac{s_1'}{s_2'}\left(1 + \frac{\Delta t}{t_1}\right)\right].$$

The travel time-difference $\Delta t$ is measured in the sound receiver E. Instead of the mean air temperature $\bar{T}_2$, the air temperature $T_{M2}$ at the microphone $M_2$ may be used as an approximation, which is the temperature at elevation $z_2$, i.e., $\overline{T}_2 \, T_{M2}$. In an approximation, the travel time $t_1$ can be calculated from the velocity of sound for dry atmospheric air at normal pressure and from the inclined path $s_1'$:

$$t_1 \approx \frac{s_1'}{331.3 + 0.6 \, (T_{M2} - 273.15)} .$$

The units of measurement are $[t_1]$=seconds, $[s_1']$=meters and $[T_{M2}]$=°K. More reliable values may be expected from the measuring of pressure, temperature, humidity, composition of air because the travel time $t_1$ of the sound pulses in the inclined path $s_1'$ depends upon these parameters of the condition of air.

In order to measure the absolute travel time $t_1$ of the sound pulses exactly, the sound emitter may be controlled by a radio channel. When the microphone $M_1$ is positioned at an elevation $z_1 = 1$ m above the ground, the mean vertical gradient of temperature $\overline{\tau}$ for 1 m elevation may be calculated from the mean difference of temperature $\Delta \overline{T}$ and the elevation $z_2$ of the microphone as follows $$\overline{\tau}_1 = \frac{\Delta \overline{T}}{\ln z_2} .$$

The mean vertical gradient of temperature $\overline{\tau}$ at any elevation $z_1$ (for instance at the elevation of the swivel axis of the tachymeter) results from the following equation:

$$\overline{\tau} = \frac{\overline{\tau}_1}{z_i} .$$

Using $\tau$, a mean local coefficient of refraction, corresponding in a way to the actual coefficient of refraction, may be calculated using known formulae.

While the invention has been disclosed and described with reference to a limited number of embodiments, it will be apparent that variations and modifications may be made therein, and it is intended in the following claims to cover each such variation and modification as falls within the true spirit and scope of the invention.

What is claimed is:

1. A measuring system for determining terrestrial refraction, comprising a geodetic measuring instrument, a device for measuring the difference of travel time of sound waves, said device for measuring the difference of travel time of sound waves comprising a sound emitter adapted to be positioned at a location remote from said measuring instrument to direct sound toward said instrument and a pair of sound receivers positioned to receive sound from said emitter along two different paths that are spaced apart at said measuring instrument for determining the difference of travel times of the sound waves, and a calculator at said measuring instrument for determining said refraction from said difference of travel time.

2. The measuring system of claim 1, wherein the sound emitter comprises a pulse generator and two electroacoustical converters mounted vertically one above the other.

3. The measuring system of claim 1, wherein the sound receivers comprise two microphones, arranged vertically one above the other, a detector for detecting the first pulse received from the sound emitter, a frequency generator, a counter, a gate circuit responsive to the pulses received by the microphones for passing oscillations of said frequency generator to said counter, and a numerical display connected to display the count of the counter.

4. The measuring system of claim 3, wherein the sound receivers further comprise a range selector connected to control the output frequency of said frequency generator, a switch connected to apply said oscillations to said gate circuit, and a control circuit for resetting said counter after a determined delay.

5. The measuring system of claim 1, wherein the sound receivers comprise two microphones arranged horizontally side-by-side, a detector for detecting the first pulse received from the sound emitter, a frequency generator, a counter, a gate circuit responsive to the pulses received by the microphones for passing oscillations of said frequency generator to said counter, and a numerical display connected to display the count of said counter.

6. A measuring system for determining terrestrial refraction, comprising a geodetic measuring instrument, and means for measuring the difference of travel times of sound waves in a pair of paths in the vicinity of said geodetic measuring instrument, said measuring means comprising a sound emitter adapted to be mounted at a position spaced from said instrument to direct sound toward said instrument, a pair of spaced apart microphones positioned adjacent said instrument to receive sound from said sound emitter along different paths that are spaced apart at said instrument, and means connected to said microphones for determining the time difference of arrival of sound from said emitter to said two microphones.

7. The measuring system of claim 6 wherein said microphones are mounted vertically one above the other, and said sound emitter comprises a single source of sound pulses whereby said microphones receive sound from said sound emitter along separate paths inclined to one another.

8. The measuring system of claim 6 wherein said means for detecting time differences comprises a detector connected to said microphones for determining which microphone receives a sound impulse first, for determining the sign of the relative time difference, a source of oscillations, a counter, gate means responsive to the receipt of sound impulses by said microphones for passing said oscillations to said counter in the time between the time of receipt of a sound impulse by one of said microphones and the time of receipt of the sound impulse by the other of said microphones, and output means connected to said counter.

9. The measuring system of claim 8 wherein said output means comprises an indicator.

10. A measuring system for determining terrestrial refraction, comprising a geodetic measuring instrument, and means for measuring the difference of travel times of sound waves in a pair of paths in the vicinity of said geodetic measuring instrument, said measuring means comprising a sound emitter, a pair of microphones positioned to receive sound from said sound emitter along different paths, and means connected to said microphones for determining the time difference of arrival of sound from said emitter to said two microphones, said geodetic instrument comprising an electronic tachymeter, said microphones being mounted on above the other on said geodetic measuring instrument.

11. A system for determining terrestrial refraction along a path between two points, comprising a geodetic measuring instrument for measuring a distance between two points, said instrument being mounted at one of said points, measuring means for measuring the difference of propagation time of sound, and comprising at least one sound transmitter at one of said points for the transmission of sound pulses and two sound receivers at the other of said points and facing the sound transmitter, the portion of said measuring means at the point at which said geodetic measuring instrument is mounted being fixedly mounted on the geodetic measuring instrument, said sound receivers being on different sides of said path and being equally spaced from said path and from said sound transmitter, and means for determining the time difference in reception of the same sound pulse between said two sound receivers.

12. The system of claim 11 wherein said sound receivers are connected to said geodetic measuring instrument.

13. The system of claim 12 wherein the sound receivers are mounted vertically one above the other.

* * * * *